United States Patent [19]

Swartz

[11] Patent Number: 4,465,075
[45] Date of Patent: Aug. 14, 1984

[54] ON-CHIP PRESSURE TRANSDUCER AND TEMPERATURE COMPENSATION CIRCUIT THEREFOR

[75] Inventor: Craig C. Swartz, Tempe, Ariz.
[73] Assignee: Motorola, Inc., Schaumburg, Ill.
[21] Appl. No.: 363,177
[22] Filed: Mar. 29, 1982
[51] Int. Cl.³ ............................................. A61B 5/02
[52] U.S. Cl. .................................. 128/672; 128/748; 128/736; 73/708
[58] Field of Search .................... 128/675, 672–673, 128/748; 73/708; 126/736

[56] References Cited

U.S. PATENT DOCUMENTS

| | | | |
|---|---|---|---|
| 2,981,911 | 4/1961 | Warnick | 128/675 X |
| 3,077,561 | 2/1963 | Revesz | 73/708 X |
| 3,196,375 | 7/1965 | Jones | 128/675 X |
| 3,831,588 | 8/1974 | Rindner | 128/675 |
| 4,264,889 | 4/1981 | Yamamoto et al. | 73/708 X |
| 4,320,664 | 3/1982 | Rehn et al. | 73/708 |
| 4,333,349 | 6/1982 | Mallon et al. | 73/708 |

FOREIGN PATENT DOCUMENTS

| | | | |
|---|---|---|---|
| 63712 | 5/1980 | Japan | 73/708 |
| 800742 | 1/1981 | U.S.S.R. | 73/708 |

Primary Examiner—Lee S. Cohen
Assistant Examiner—Angela D. Sykes
Attorney, Agent, or Firm—William E. Koch

[57] ABSTRACT

An integrated circuit including a pressure transducer is disclosed for temperature compensating the output voltage thereof with respect to undesirable temperature induced signals from the pressure transducer. A resistor in series with the pressure transducer controls the span of the output voltage. A plurality of resistors in parallel with the pressure transducer serve as a voltage divider for adjusting the output voltage at zero for zero pressure. Silicon resistors serving as thermistors in the voltage divider may be added to the circuit by laser cutting shorting links for temperature compensating the offset.

8 Claims, 1 Drawing Figure

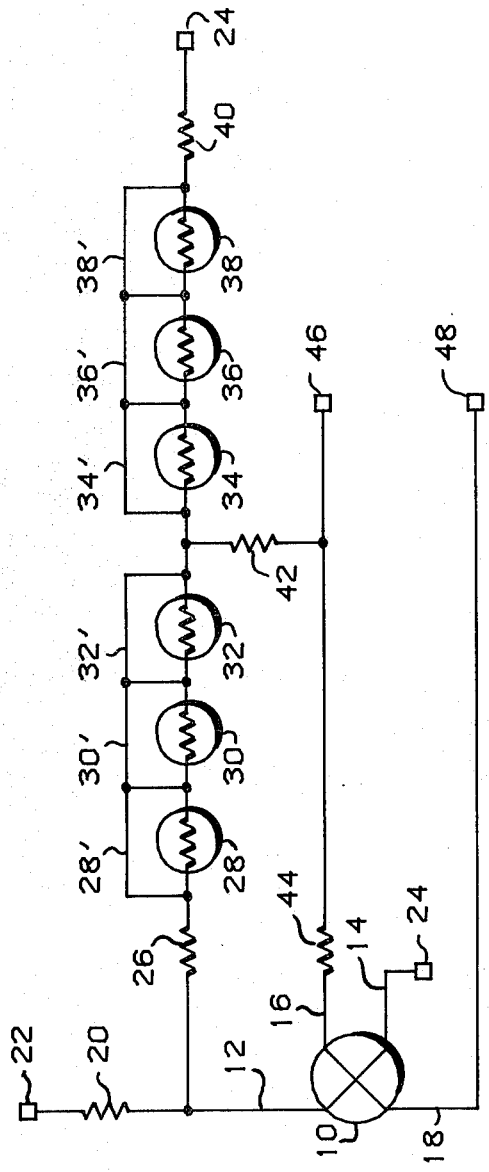

ON-CHIP PRESSURE TRANSDUCER AND TEMPERATURE COMPENSATION CIRCUIT THEREFOR

BACKGROUND OF THE INVENTION

1. Field of the Invention

This invention relates generally to pressure sensors, and more particularly, to integrated circuit pressure transducers having on chip circuitry that compensates for voltage shifts in the output of the pressure transducer due to changes in temperature.

2. Background Art

Numerous medical and industrial applications require an electronic pressure measurement that is relatively inexpensive, accurate over a limited temperature range, and requires little space. One such application involves measuring a person's blood pressure by placing a small pressure transducer in a saline solution that is connected intravenously to the person's circulatory system. The output of the pressure transducer is connected to an apparatus that displays the blood pressure visually.

Unfortunately, most semiconductor pressure transducers have undesirable temperature characteristics which are different for different transducers. Offset voltage, which is the differential output voltage of the transducers at zero pressure, not only varies in magnitude for different transducers, but also varies with temperature change. Also, the temperature coefficient of "span", or change in voltage output versus change in pressure, typically has a negative value, the range of values varying for both different transducers and changes in temperature.

One known configuration for temperature compensation of span is a temperature compensation circuit that utilizes a plurality of thermistors which vary the magnitude of the excitation voltage across the transducer to compensate for the undesirable changes in sensitivity with temperature. The pressure transducer is basically a bridge circuit and the thermistors are connected from each input terminal of the bridge to a power supply line. The thermistors change the excitation voltage level so that the output voltage across the terminals of the bridge remain constant for a given change in pressure even though the temperature changes. The thermistors have been shunted with temperature stable elements such as resistors to tailor the compensation characteristic. The combination of resistors, thermistors, and transducer has been adjusted by laser trimming through iterative operations over temperature to provide a composite device having a desired degree of temperature independence. These adjustments include sequential measurements over temperature and trimming. These elements can also be trimmed to compensate for the undesired temperature dependence of the transducer offset voltage.

Another known configuration requires the insertion of jumpers or connecting wires to complete parts of the circuit. The circuit must be tested with each individual transducer to determine whether the temperature coefficient of offset is positive or negative and then a jumper inserted to have the circuit compensate appropriately. The inclusion of jumpers results in a major cost increase. Furthermore, the procedure for inserting the jumpers induces inaccuracies into the circuit. The jumper insertion device picks up radio frequency interference from the laser used for trimming the resistors and typically induces up to 30 millivolts into the output of the circuit.

Yet another known configuration utilizes a compensating means having two thermistors. The thermistors are coupled to a high and low side of the voltage source, respectively, and each provide a signal to the excitation terminal of the pressure transducer. The pressure transducer output is summed with the signals from both thermistors, the summation thereafter being amplified.

The above configurations require negative temperature coefficient thermistors which cannot be placed on a chip of an integrated circuit. Furthermore, the known configurations may require a complex procedure for trimming the resistors. The gain of the circuit and the offset voltage of the transducer interact, requiring different pressures for setting both. Thus, the need exists for a temperature compensating pressure transducer circuit that, along with the pressure transducer, is an integrated circuit that does not use negative coefficient thermistors, does not have jumpers and wherein gain and transducer offset do not interact thereby simplifying the resistor trimming procedure.

SUMMARY OF THE INVENTION

Accordingly, it is an object of this invention to provide an improved on-chip temperature compensation circuit for pressure transducers.

A further object of this invention is to provide an improved on-chip pressure transducer wherein the span, offset, and temperature compensation of offset are adjustable.

In carrying out the above and other objects of the invention in one form, there is provided an improved integrated circuit having first and second voltage conductors and first and second circuit output conductors for measuring changes in pressure. The circuit comprises a pressure transducer having first and second pressure transducer input conductors and first and second pressure transducer output conductors, wherein the second pressure transducer input conductor is coupled to the second voltage conductor and the second pressure transducer output conductor is coupled to the second circuit output conductor. A resistor is coupled between the first pressure transducer output conductor and the first circuit output conductor. A means is coupled to the first voltage conductor and the first pressure transducer input conductor for adjusting the span of the voltage output at the first and second circuit output conductors. A means for adjusting the offset at the first and second circuit output conductors includes a first offset means coupled between the first pressure transducer input conductor and the first circuit output conductor and a second offset means coupled between the first circuit output conductor and the second voltage conductor. A means for temperature compensating the offset includes a first temperature compensation means coupled between the first pressure transducer input conductor and the first circuit output conductor and a second temperature compensation means coupled between the first circuit output conductor and the second voltage conductor.

The above and other objects, features, and advantages of the present invention will be better understood from the following detailed description taken in conjunction with the accompanying drawing.

BRIEF DESCRIPTION OF THE DRAWING

The single drawing is a schematic of one embodiment of the invention.

DETAILED DESCRIPTION OF THE INVENTION

Pressure transducers typically are a piezoresistive pressure sensing element such as a single resistor having taps on four sides or a bridge circuit having four resistive elements. An excitation voltage is applied to two input terminals with an output voltage appearing at two output terminals. As pressure is applied to the pressure transducer, the output voltage will vary. However, pressure transducers have inherent problems including zero pressure output, temperature coefficient of offset, and temperature coefficient of span.

Temperature coefficient of offset refers to the varying of output voltage at zero pressure as temperature varies. Temperature coefficient of span refers to the change in output voltage versus change in pressure and typically has a negative value with the range varying for both different pressure transducers and changes in temperature.

Referring now to the single figure, there is illustrated in schematic form a temperature compensation integrated circuit that eliminates the inherent problems of the pressure transducer 10 as discussed hereinabove. The circuit may also be fabricated with discrete elements and is not to be limited to an integrated circuit. Pressure transducer 10 has excitation conductors 12 and 14 and positive and negative output conductors 16 and 18, respectively. Resistor 20 is coupled between positive power supply pad 22 and excitation conductor 12, for adjusting the excitation voltage across pressure transducer 10. Excitation conductor 14 is connected to negative power supply pad 24. Negative power supply pad 24 may, alternatively, be ground.

One side of positive offset resistor 26 is connected to excitation conductor 12. The other side of resistor 26 is connected to thermistor 28. Thermistors 28, 30, 32, 34, 36, and 38 are connected in series and are coupled between resistor 26 and negative offset resistor 40. The other side of resistor 40 is connected to negative power supply pad 24. Positive and negative offset resistors 26 and 40 may be trimmed to adjust the output voltage at conductors 16 and 18 to zero for zero pressure. Although resistor 26, thermistors 28, 30, 32 are shown in series, and resistor 40, thermistors 34, 36, 38 are shown in series, the invention is not to be so limited. Thermistors 28, 30, 32, as well as thermistors 34, 36, 38, may be in parallel with each other and may also be in parallel with resistors 26 and 40 respectively. Any series or parallel combination may be used.

Thermistors 28, 30, 32, 34, 36, and 38 are typically resistors made of silicon and have a positive temperature coefficient of resistance. As the temperature of thermistors 28, 30, 32, 34, 36, and 38 increases, their resistance increases. Each of thermistors 28, 30, 32, 34, 36, and 38 have a shorting link 28', 30', 32', 34', 36', and 38' connected in parallel therewith. Shorting links 28', 30', 32', 34' 36' and 38' bear the prime designation for ease of identifying the respective thermistor 28, 30, 32, 34, 36, and 38. For instance, thermistor 28 has shorting link 28' coupled across the sides thereof, so that all current is diverted from the thermistor 28 through the shorting link 28'. Shorting links 28', 30', 32', 34', 36' and 38' comprise a material, aluminum for example, whose current path may permanently be interrupted, such as by cutting with a laser beam. When an aluminum shorting link is cut, the associated thermistor will be "added" to the circuit. The addition of thermistors 28, 30, 32, 34, 36, and 38 provide for control of the temperature compensation of offset and will be discussed in greater detail hereinafter.

One side of resistor 42 is connected between thermistors 32 and 34 and associated shorting links 32' and 34'. The other side of resistor 42 is connected to one side of resistor 44 and output pad 46. Resistor 42 may be eliminated from the circuit by increasing the resistance of resistors 26 and 40, and replacing resistor 42 with a conductor. The other side of resistor 44 is connected to output conductor 16. Output conductor 18 of pressure transducer 10 is connected to output pad 48.

Under quiescent, or zero pressure conditions, output conductors 16 and 18 are biased to have 0–20 millivolts thereacross for the typical case where positive power supply pad 22 has 5–10 volts applied thereto. As pressure is applied to transducer 10, the magnitude of the voltage at output conductor 16 tends to increase and the magnitude of the voltage at output conductor 18 tends to decrease thereby creating a differential output voltage therebetween. Unfortunately, the span of transducer 10 tends to decrease with increase in temperature. This means that as the temperature increases, a given change in pressure on transducer 10 will produce less differential voltage between terminals 16 and 18. This change in differential voltage due to pressure is nearly linear over the pressure range of interest.

Pressure transducers can be of various types by way of their construction or design. Different types of transducers 10 can have different negative coefficients of span. Thus, resistor 20 may be adjusted for each type of transducer to compensate for the change in span with temperature by adjusting the magnitude of the excitation voltage at terminals 12 and 14 with temperature which affects the differential output voltage between terminals 16 and 18. For transducers of the same type, the span can be compensated over a temperature range of between zero degrees centigrade to 75 degrees centigrade, for example, to provide a variation in transducer output voltage at any pressure of interest within accuracy of 2% of full scale.

Resistors 26, 40, 42, 44, serve as a voltage divider for compensating the offset by setting the zero pressure voltage at output pads 46 and 48. The voltage at output pads 46 and 48 may be set at zero for zero pressure by trimming offset resistor 26 or resistor 40 and causing the voltage drop across resistor 44 to equal the voltage drop across output conductors 16 and 18 of pressure transducer 10.

In order to maintain zero volts at output pads 46 and 48 for zero pressure on transducer 10 as temperature is varied, the thermistors 28, 30, 32, 34, 36, and 38 may be "added" to the circuit by cutting out shorting links 28', 30', 32', 34', 36', and 38'. The thermistors 28, 30, 32, 34, 36, and 38 have different values of resistance which are predetermined wherein a combination may be selected for compensating the negative or positive coefficient of offset of the transducer 10.

By now it should be appreciated that there has been provided an improved temperature compensation circuit for pressure sensors. This circuit may be manufactured as an integrated circuit by using positive temperature coefficient resistors and does not require the complex procedure of inserting jumpers.

I claim:

1. A circuit having first and second voltage conductors and first and second circuit output conductors for measuring changes in pressure, said circuit comprising:
   a pressure transducer having first and second pressure transducer input conductors and first and second pressure transducer output conductors, said second pressure transducer input conductor coupled to said second voltage conductor, said second pressure transducer output conductor coupled to said second circuit output conductor;
   a first resistor coupled between said first pressure transducer output conductor and said first circuit output conductor;
   means coupled to said first voltage conductor and said first pressure transducer input conductor for adjusting the span of the output at said first and second circuit output conductors;
   means for adjusting the offset at said first and second circuit output conductors including a first offset means coupled between said first pressure transducer input conductor and said first circuit output conductor and a second offset means coupled between said first circuit output conductor and said second voltage conductor; and
   means for temperature compensating the offset including a first temperature compensation means coupled between said first pressure transducer input conductor and said first circuit output conductor and a second temperature compensation means coupled between said first circuit output conductor and said second voltage conductor.

2. The circuit according to claim 1 wherein said first and second temperature compensation means each comprise a plurality of positive temperature coefficient resistors and a plurality of shunting means, one of said shunting means coupled across one of each of said positive temperature coefficient resistors wherein a predetermined number of said shunting means may be disabled in order to enable the respective one of said positive temperature coefficient resistors.

3. The circuit according to claim 1 wherein said means for adjusting the span is a resistor that may be trimmed to compensate for the resistance of said pressure transducer.

4. The circuit according to claim 1 wherein said first and second offset means are resistors that may be trimmed to compensate for the resistance of said pressure transducer.

5. A temperature compensation circuit having first and second voltage conductors and first and second circuit output conductors, for temperature compensating an output voltage of a pressure transducer having first and second pressure transducer input conductors and first and second pressure transducer output conductors, said circuit comprising:
   a first trimable resistor coupled between said first voltage conductor and said first pressure transducer input conductor, said second voltage conductor coupled to said second pressure transducer input conductor;
   a second resistor coupled between said first pressure transducer output conductor and said first circuit output conductor, said second pressure transducer output conductor coupled to said second circuit output conductor;
   a third trimable resistor having a first side coupled to said first pressure transducer input conductor;
   a fourth trimable resistor having a first side coupled to said second voltage conductor;
   a plurality of first positive temperature coefficient resistors coupled between a second side of said third resistor and said first circuit output conductor; and
   a plurality of second positive temperature coefficient resistors coupled between a second side of said fourth resistor and said first circuit output conductor, wherein a predetermined number of said first and second positive temperature coefficient resistors may be enabled in order to substantially compensate for the temperature coefficient of said pressure transducer.

6. The temperature compensation circuit according to claim 5 further comprising a fifth resistor coupled between said first circuit output conductor and a node located between said first and said second positive temperature coefficient resistors.

7. An integrated circuit having a first and a second voltage conductor and a first and a second circuit output conductor, for measuring blood pressure, comprising:
   a pressure transducer having first and second pressure transducer input conductors and first and second pressure transducer output conductors, said second pressure transducer input conductor coupled to said second voltage conductor, said second pressure transducer output conductor coupled to said second circuit output conductor, said pressure transducer sensing said blood pressure and providing a representative voltage at said first and second pressure transducer output conductors;
   a first resistor coupled between said first pressure transducer output conductor and said first circuit output conductor;
   means coupled to said first voltage conductor and said first pressure transducer input conductor for adjusting the span of the output at said first and second circuit output conductors;
   means for adjusting the offset at said first and second circuit output conductors including a first offset means coupled between said first pressure transducer input conductor and said first circuit output conductor and a second offset means coupled between said first circuit output conductor and said second voltage conductor; and
   means for temperature compensating the offset including a first temperature compensation means coupled between said first pressure transducer input conductor and said first circuit output conductor and a second temperature compensation means coupled between said first circuit output conductor and said second voltage conductor.

8. The circuit according to claim 7 wherein said first and second temperature compensation means each comprise a plurality of positive temperature coefficient resistors and a plurality of shunting means, one of said shunting means coupled across one of each of said positive temperature coefficient resistors wherein a determined number of said shunting means may be disabled in order to enable the respective one of said positive temperature coefficient resistors.

* * * * *